(12) United States Patent
Healy et al.

(10) Patent No.: US 6,613,075 B1
(45) Date of Patent: Sep. 2, 2003

(54) RAPID EXCHANGE SELF-EXPANDING STENT DELIVERY CATHETER SYSTEM

(75) Inventors: Stephen R. Healy, Miami, FL (US); Mark N. Inderbitzen, Miramar, FL (US)

(73) Assignee: Cordis Corporation, Miami Lakes, FL (US)

(*) Notice: Subject to any disclaimer, the term of this patent is extended or adjusted under 35 U.S.C. 154(b) by 0 days.

(21) Appl. No.: 09/571,477

(22) Filed: May 16, 2000

Related U.S. Application Data

(60) Provisional application No. 60/161,862, filed on Oct. 27, 1999.

(51) Int. Cl.[7] .................................................. A61F 2/06
(52) U.S. Cl. ...................................... 623/1.11; 606/108
(58) Field of Search ................................. 604/302, 264, 604/523, 103.04; 606/108; 623/1.11

(56) References Cited

U.S. PATENT DOCUMENTS

| 4,732,152 A | 3/1988 | Wallstén et al. |
| 5,690,644 A | 11/1997 | Yurek et al. |
| 5,843,176 A | 12/1998 | Weier |
| 5,968,070 A | 10/1999 | Bley et al. |
| 6,019,778 A | 2/2000 | Wilson et al. |
| 6,117,140 A | * 9/2000 | Munsinger .................. 606/108 |

OTHER PUBLICATIONS

Pfizer, Schneider Worldwide 89006D/11.97/10, "Wallstent Endoprosthesis Magic Wallstent Device"; Instruction For Use brochure.

* cited by examiner

Primary Examiner—Corrine McDermott
Assistant Examiner—Thomas Barrett

(57) ABSTRACT

A self-expanding stent delivery system for medical treatment of a patient has a rapid exchange configuration. The system includes a stent, a proximal and distal shaft section, a cartridge for holding the stent compressed until deployment, a stabilizer for holding the stent in position as an outer sheath is retracted, and a flexible tapered introducer tip. The stent is mounted about the distal shaft section and compressed to an initial diameter within the cartridge. The introducer tip is affixed to the distal end of the catheter system. A guidewire may be back-loaded into a distal port at the catheter system distal end. The guidewire extends through a guidewire tube through the location of the stent, and escapes through a proximal guidewire port, which is located at a point intermediate the catheter system proximal and distal ends.

17 Claims, 6 Drawing Sheets

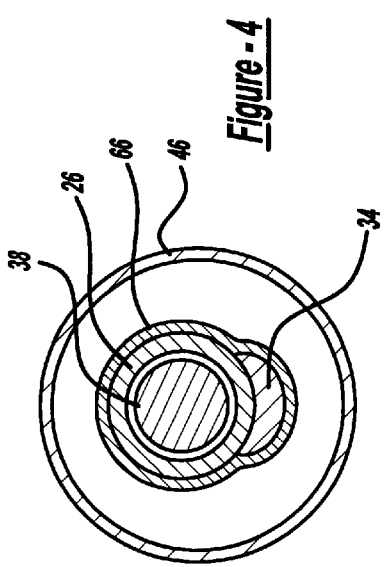
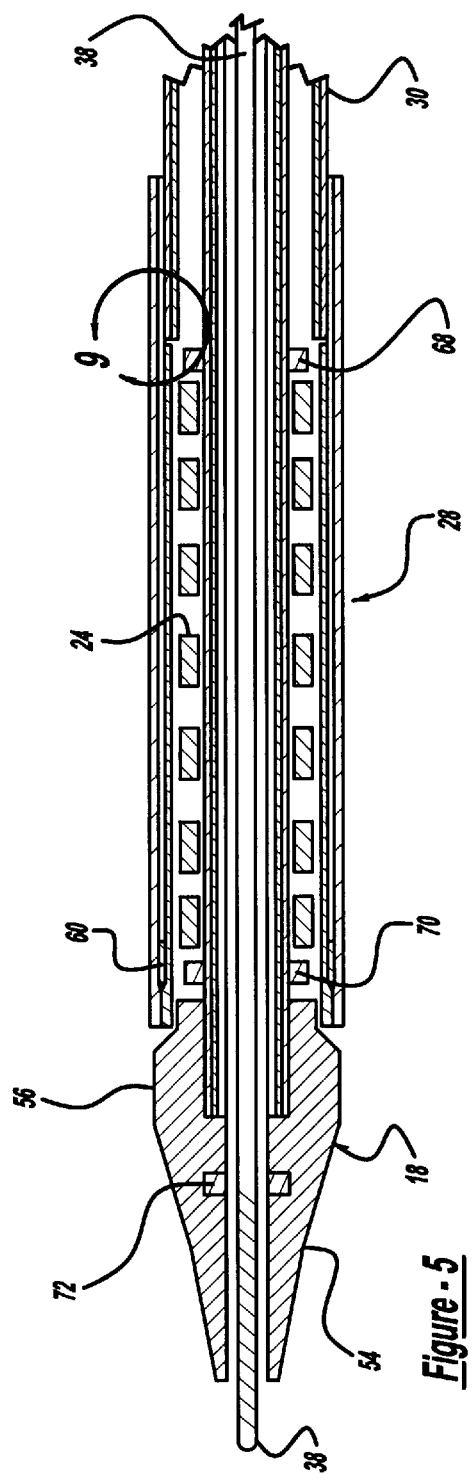

RAPID EXCHANGE SELF-EXPANDING STENT DELIVERY CATHETER SYSTEM

CROSS-REFERENCE To RELATED APPLICATION

This application claims priority of U.S. Provisional Patent Application No. 60/161,862, filed Oct. 27, 1999.

BACKGROUND AND SUMMARY OF THE INVENTION

1. Technical Background

The present invention relates generally to medical devices, and more particularly to a self-expanding stent delivery catheter system having a rapid exchange configuration.

2. Discussion

Catheter systems are used in a variety of therapeutic applications, including many vascular treatments. Various types of catheters are available, such as balloon catheters for procedures such as angioplasty. Angioplasty can be used to treat vascular disease, in which blood vessels are partially or totally blocked or narrowed by a lesion or stenosis.

In many instances of vascular disease, a local area of a blood vessel may become narrowed. This narrowing is called a lesion or stenosis, and may take the form of hard plaque, cholesterol, fats, or viscous thrombus. Such a stenosis may cause heart attack or stroke, which are significant health problems affecting millions of people each year. Typical disease patterns involve stenosis development, causing a blockage or partial blockage at the site.

For example, various procedures are well known for addressing stenoses and opening body vessels that have a constriction due to plaque buildup or thrombus, etc. With such procedures, an expansive force may be applied to the lumen of the stenosis. This outward pressing of a constriction or narrowing at the desired site in a body passage is intended to partially or completely re-open or dilate that body passageway or lumen, increasing its inner diameter or cross-sectional area. In the case of a blood vessel, this procedure is referred to as angioplasty. The objective of this procedure is to increase the inner diameter or cross-sectional area of the vessel passage or lumen through which blood flows, to encourage greater blood flow through the newly expanded vessel.

Often, it is deemed to be desirable to leave a device in place at the site of the expanded lumen of the stenosis, to provide support for the vessel wall at that location. Such a device may provide a scaffold type of structure about which, for example, endothelium development can occur to help repair the diseased, injured or damaged area. This scaffold device is referred to as a stent or endoprosthesis, and may have various designs, often having a resilient, flexible and cylindrical spring shape. In some cases, the stent which is a flexible cylinder or scaffold made of metal or polymers may be permanently implanted into the vessel. The stent tends to hold the lumen open longer, to reinforce the vessel wall and improve blood flow.

Stenting has come to be an accepted interventional medical procedure in many situations where vessels require support on a long-term basis. In operation, a catheter is used to transport the stent into and through a blood vessel, until the stent or the like is positioned at a desired location. Once at the desired location, the stent is deployed to provide internal support of the vessel or other treatment.

Some stents are deployed by an angioplasty balloon catheter, either during the angioplasty procedure or after a balloon has opened up the stenosis. These are called balloon-deployed or balloon-expandable stents. The balloon-expandable stents are forcibly expanded by a balloon or similar device through plastic deformation of the stent from a smaller to a larger diameter.

Another type of stent is of the self-expanding variety. Self-expanding stents tend to resiliently expand from an initial diameter, and must be held constantly in compression to remain at the initial diameter during delivery. Typically, a single cylindrical sheath or similar device over the stent is needed to hold the stent or other endoprosthesis at an initial diameter during passage through the body vessel. Once the treatment site is reached, the sheath or other device is withdrawn from around the stent, and the stent resiliently expands in place of its own accord.

This invention generally relates to stents which are of the self-expanding type. More particularly, the invention relates to self-expanding stents or other endoprostheses delivered in a compressed condition under radial compression, and which are deployed by removing a restraining member to permit the stent to resiliently expand and support a body vessel at that location. The stent may be made of a continuous strand shaped as a generally cylindrical member and having a plurality of coiling and/or undulating spring portions wound from the strand so as to impart the desired radial expansion force. The stent may also be formed of a metal or polymer tube, with cuts or slits removed to form a lattice.

As an example, the present invention will be described in relation to coronary, peripheral, and neurological vascular stenting treatments. The coronary procedure is often referred to as "coronary stenting." However, it should be understood that the present invention relates to any rapid exchange stent delivery system having the features of the present invention, and is not limited to a particular stent design or a particular deployment location.

Some catheters have a relatively long and flexible tubular shaft defining one or more passages or lumens, and may deliver and deploy the stent near one end of the shaft. This end of the catheter where the stent is located is customarily referred to as the "distal" end, while the other end is called the "proximal" end. The proximal end of the shaft may lead to a hub coupling for connecting the shaft and the lumens to various equipment. Examples of stents and catheters are shown in U.S. Pat. No. 5,843,176, entitled "Self-Expanding Endoprosthesis," issued to Weier on Dec. 1, 1998; and also U.S. Pat. No. 5,968,070, entitled "Covered Expanding Mesh Stent," issued to Bley et al. on Oct. 19, 1999. In addition, U.S. Pat. No. 6,019,778 to Wilson et al., entitled "Delivery Apparatus For A Self-Expanding Stent" describes a self-expanding stent delivery system.

A common treatment method for using such a catheter is to advance the catheter into the body of a patient, by directing the catheter distal end percutaneously through an incision and along a body passage until the stent is located within the desired site. The term "desired site" refers to the location in the patient's body currently selected for treatment by a health care professional. After the stent is deployed within the desired site, it will tend to resiliently expand to press outward on the body passage.

It is of course desirable to retain the stent securely in the proper position. The stent delivery system should also preferably protect the stent from damage or deformation during delivery. It is further desirable that the stent delivery system should be flexible and able to push through and traverse as many different anatomical arrangements and stenosis configurations as possible. Moreover, the stent delivery system should preferably have a positive mechanism for holding and then releasing and deploying the stent at the desired site. The stent delivery system also desirably includes a mechanism for securing the stent in the form of a sheath, capable of completely covering the compressed stent during insertion.

Stent delivery systems are often designed for the smallest possible outer diameter or profile at the distal end. This small profile may be preferred for access into small vessels following angioplasty, or during a procedure called "direct stenting" where no angioplasty is performed.

In addition, the stent delivery system should provide for high visibility under fluoroscopy. Often the stent delivery system will be used in conjunction with an outer guiding catheter, which surrounds and guides the stent delivery system to the desired site. The visibility of the stent delivery system on a fluoroscope may be affected by the size of the lumen through which radiopaque contrast fluid is injected. This fluid is generally injected through the annular space between the guiding catheter and the stent delivery system. The visibility can therefore preferably be increased by further reducing the outer diameter of the stent delivery system.

Like many catheter systems, a stent delivery system is often used with a flexible guidewire. The guidewire is often metal, and is slidably inserted along the desired body passage. The catheter system is then advanced over the guidewire by "back-loading" or inserting the proximal end of the guidewire into a distal guidewire port leading to a guidewire lumen defined by the catheter system.

Many catheter systems define guidewire lumens that extend along the entire length or almost all of the catheter. These catheter systems are described as "over-the-wire" catheters, in that the guidewires revisions inside a catheter lumen throughout the length of the catheter. Over-the-wire catheter systems provide several advantages, including improved trackability, preventing prolapse of the guidewire, the ability to flush the guidewire lumen while the catheter is in the patient, and the capability of easily removing and exchanging the guidewire while retaining the catheter in a desired position in the patient.

In some circumstances it may be desirable to provide a "rapid-exchange" catheter system, which offers the ability to easily remove and exchange the catheter while retaining the guidewire in a desired position within the patient. In the balloon catheter arena, rapid exchange balloon catheters are disclosed in U.S. Pat. Nos. 5,380,283 and 5,334,147 to Johnson on Jan. 10, 1995 and Aug. 2, 1994, both entitled "Rapid Exchange Type Dilatation Catheter." Also, U.S. Pat. No. 5,531,690 to Solar on Jul. 2, 1996, entitled "Rapid Exchange Catheter" describes a rapid exchange balloon catheter, as does U.S. Re. Pat. No. 36,104 to Solar entitled "Dilation Catheter With Eccentric Balloon."

In other words, rapid-exchange balloon dilatation catheters are capable of advancement into the vascular system of a patient along a pre-positioned guidewire, for balloon angioplasty or a similar procedure. The guidewire occupies a catheter lumen extending only through a distal portion of the catheter. With respect to the remaining proximal catheter portion, the guidewire exits the internal catheter lumen through a proximal guidewire port, and extends in parallel along the outside of the catheter proximal portion. Of course, the entire catheter and guidewire assembly is typically contained within the lumen of a guiding catheter, which retains a majority of the catheter and guidewire effective lengths together.

Because a majority of the guidewire is outside the catheter shaft, it may be manually held in place as the catheter is removed. Because the distal catheter guidewire lumen is shorter than the guidewire length that remains outside the patient, the catheter may be removed while also holding the guidewire, until the guidewire may be grasped at a point distal of the catheter. Completing a catheter exchange simply requires reversing the removal process. This rapid exchange technique enables a single physician to exchange balloon catheters, without requiring guidewire extension to temporarily double the guidewire length.

It may also be desirable to provide a self-expanding stent delivery system with a rapid exchange configuration. Prior self-expanding stent delivery systems are generally of the over-the-wire type. Such over-the-wire self-expanding stent delivery system includes an inner tubular body defining a guidewire lumen and providing a spine around which a compressed stent is mounted, as well as an outer sheath for containing the stent until it is pulled proximally to release the stent.

In contrast, most rapid exchange catheter systems incorporate a proximal guidewire port located at an intermediate point, between the catheter proximal and distal ends. However, the guidewire tube of a self-expanding stent delivery system is often surrounded by an outer sheath that must be capable of sliding motion to release the stent. Thus, a port or opening through both inner and outer tubes presents some alignment challenges, because the respective ports through the inner and outer tubes will tend to shift away from each other as the outer sheath is retracted.

One possible design is described in U.S. Pat. No. 5,690,644 to Yurek et al., entitled "Apparatus For Deploying Body Implantable Stent." Yurek et al. teaches a groove along an interior catheter that extends proximally to the proximal end of the catheter which cooperates with a long slot in the exterior catheter that likewise runs to the proximal end of the catheter. However, such a long groove and slot may tend to cause weakness in bending or pull strength. Unnecessary irritation of the vasculature may also be possible.

Accordingly, the present invention preferably provides a stent delivery system having a rapid exchange configuration for delivering and deploying a self-expanding stent. Among many kinds of modifications and features that may be provided with the stent delivery system of the present invention are a relatively small profile, several radiopaque marker bands indicating the positions of certain components, flexibility, minimization of any sharp edges when advancing or withdrawing the catheter system or when retracting the outer sheath, optimized longitudinal force transmission, materials selected for performance, affirmative release of the self-expanding stent when the sheath is retracted, as well as the safe and certain back-loading of a guidewire through the distal guidewire port and out the proximal guidewire port. Any shifting of the relative positions of the proximal ports in the inner and outer tubes should also be acceptably provided for. This stent delivery system preferably also provides stent position retention, as well as stent protection, during insertion of the catheter.

The stent delivery system also preferably has a high visibility arrangement for the injection of radiopaque contrast medium, facilitated by the relatively small reduced outer diameter of the stent delivery system including the sheath.

These and various other objects, advantages and features of the invention will become apparent from the following description and claims, when considered in conjunction with the appended drawings.

BRIEF DESCRIPTION OF THE DRAWINGS

FIG. 4 is a transverse cross-section view of the stent delivery system of FIG. 3;

FIG. 5 is a partial longitudinal cross-section view of a stent delivery system arranged according to the principles of the present invention;

DETAILED DESCRIPTION OF THE PREFERRED EMBODIMENT

Figure 1:
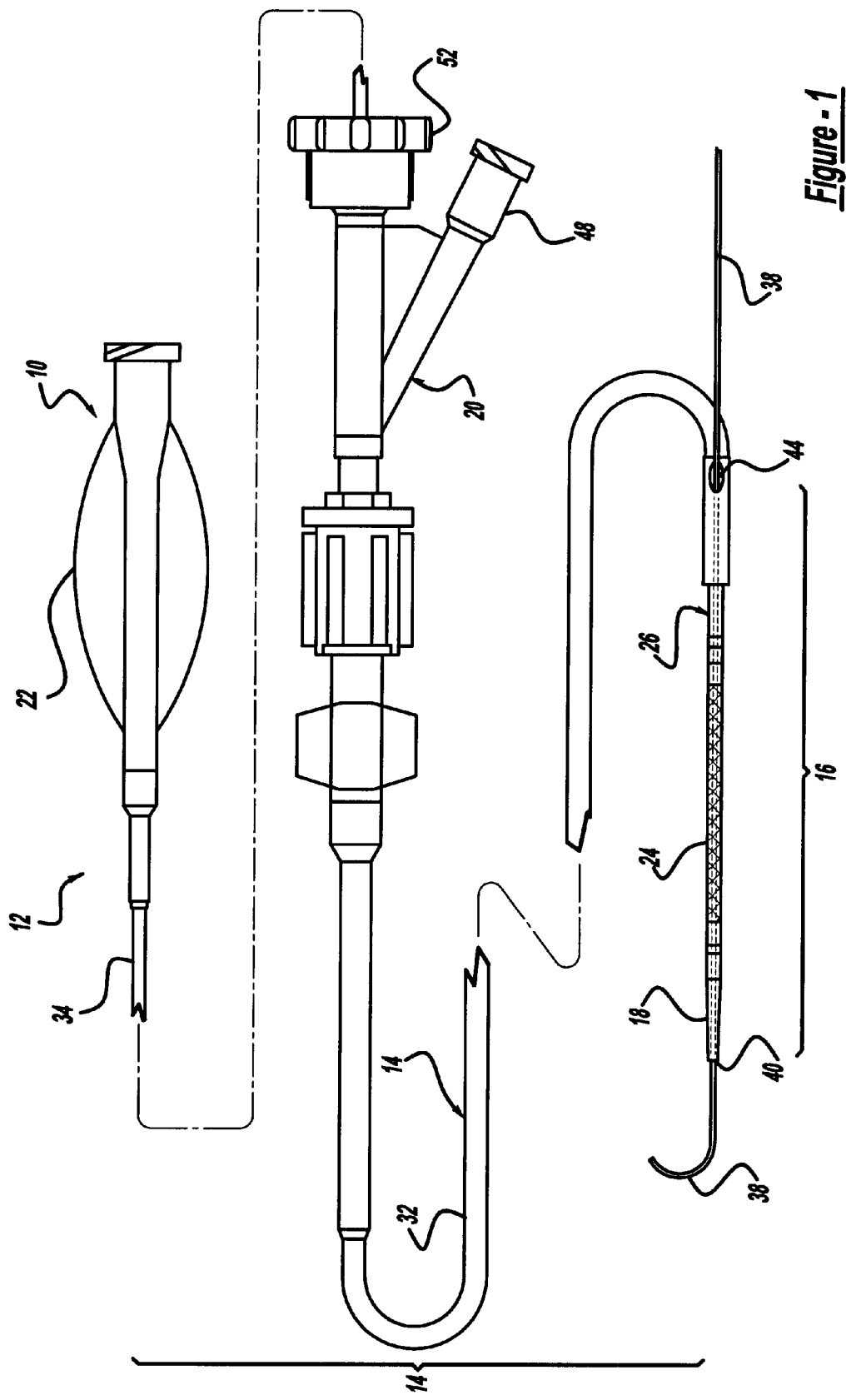
FIG. 1 is an external diagrammatic view of a stent delivery system, arranged according to the principles of the present invention.
Figure 2:
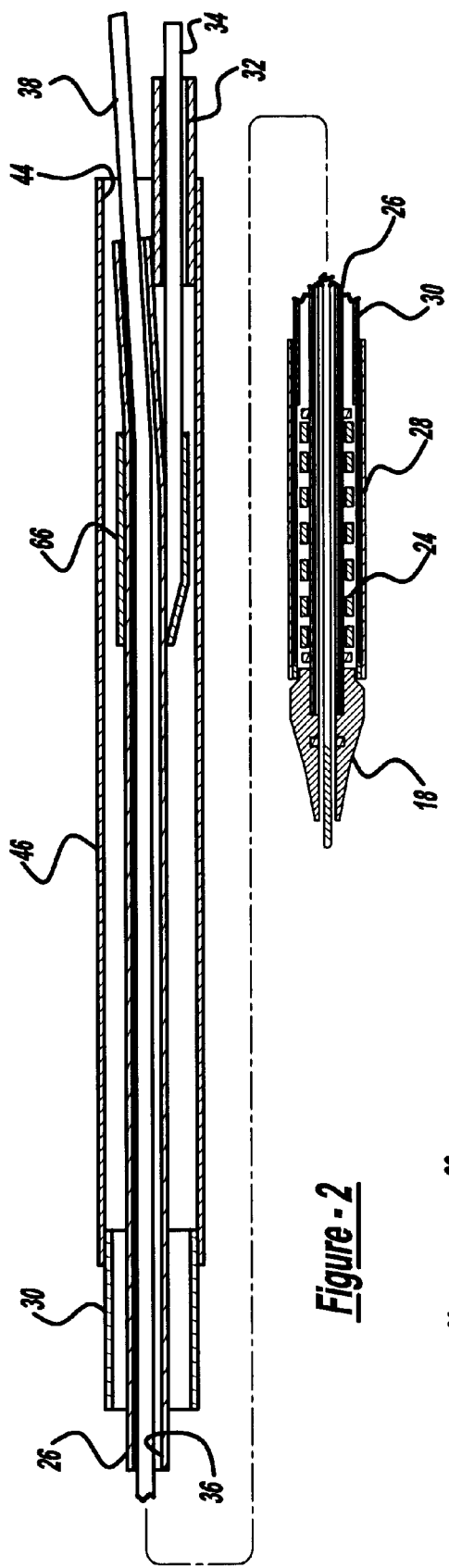
FIG. 2 is a partial longitudinal cross-section view of the stent delivery system of FIG. 1, shown in an initial configuration.
Figure 3:
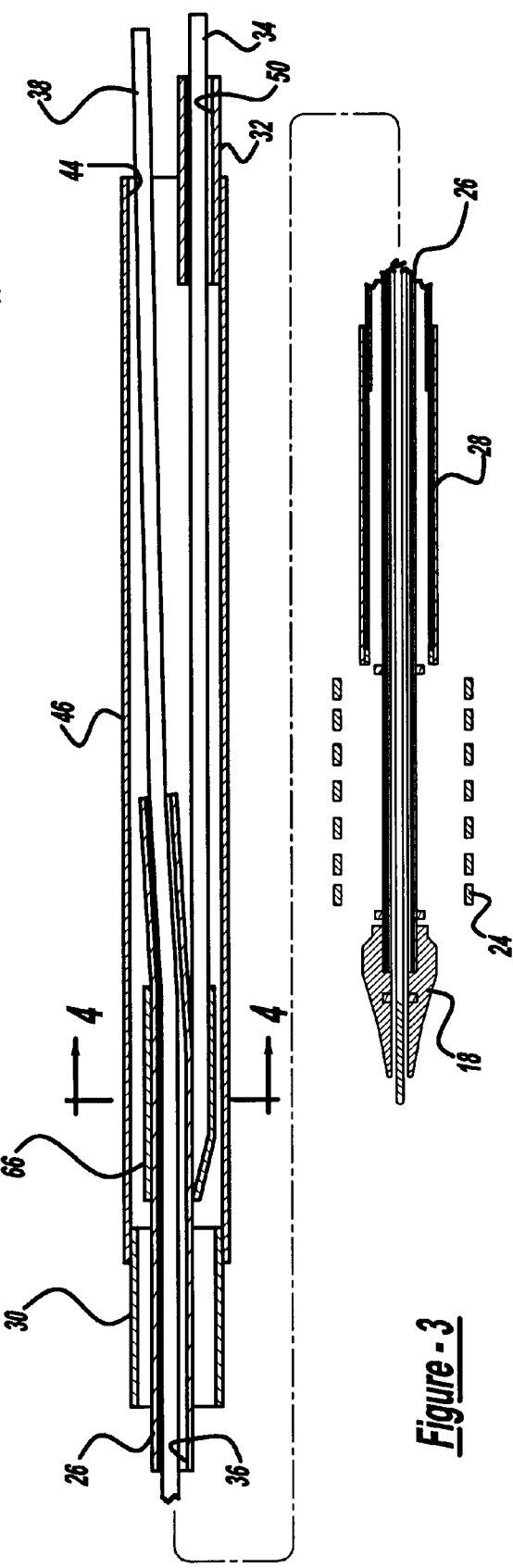
FIG. 3 is a partial longitudinal cross-section view of the stent delivery system of FIG. 2, wherein the sheath is partially retracted and the stent released.

The following description of the preferred embodiments of the present invention is merely illustrative in nature, and as such it does not limit in any way the present invention, its application, or uses. Numerous modifications may be made by those skilled in the art without departing from the true spirit and scope of the invention.

Referring to the drawings, a stent delivery system is depicted, with one of the preferred embodiments of the present invention being shown generally at 10. The illustrated stent delivery catheter system depicts of course only one of many different catheter system designs within the scope of the present invention.

In the illustrated embodiment, the stent delivery system 10 shown in the drawings consists of a catheter system 12 including a proximal and distal shaft section 14 and 16, a tapered distal tip 18, a first and second proximal hub 20 and 22, and a stent 24. The distal shaft section 16 may preferably include an inner tubular body 26, the self-expanding stent 24 compressed around the inner body 26 which is held compressed in place by a tubular cartridge 28, the flexible tapered introducer tip 18, and an outer body sheath 30. The proximal shaft section 14 may preferably include a proximal shaft tube 32, a stabilizing wire 34, and the first and second proximal hubs 20 and 22.

The present stent delivery system designs provide a guidewire lumen 36 for slidably receiving a long flexible guidewire 38, extending from a distal port 40 defined by the distal tip 18, through the inner body 26 to an inner proximal port 42 defined at the proximal end of the inner body 26, and out an outer proximal port 44 defined at the distal end of the proximal shaft tube 32.

The present stent delivery system thus has a configuration referred to as rapid-exchange, because the proximal guidewire port is located at an intermediate position. In comparison, an over-the-wire configuration provides a proximal guidewire port located in the proximal hub, such that the guidewire would be enclosed within the catheter shaft for the full length of the catheter. The present rapid exchange design provides the advantage of removing and exchanging the catheter 12 without removing the guidewire 38.

An intermediate transition tube 46 couples the proximal shaft tube 32 to the distal outer body 30, and provides a transition from the coaxial distal shaft section 16 and the proximal shaft section 14. As with all mechanical interfaces of the present stent delivery system, those of average skill in the art will be well aware of various methods of coupling components, including adhesives, heat-welding, interference close fit, snap-lock, a combination of known methods, etc.

The first proximal hub 20 is affixed to the proximal end of the proximal shaft tube 32. The first hub 20 also provides a maneuvering handle for a physician, as well as a flush port 48. The flush port 48 may have a coupling accompanied by a luer-lock fitting for connecting a flush lumen 50 to a source of pressurized inflation fluid (not shown) in the conventional manner. The first hub 20 may also include a screw-down locking device 52 to selectively lock down the stabilizing wire 34. The first hub 20 may also have a hemostatic valve (not shown) for slidably sealing the lumen 50 around the stabilizing wire 34. The proximal shaft tube 32 defines one or more passages such as flush lumen 50, connected at its proximal end to the first hub 20 and at its distal end to the transition tube 46.

The stabilizing wire 34 extends through and slides within the proximal shaft tube 32, out through the first hub 20, and is connected to the second proximal hub 22. At its distal end, the stabilizing wire 34 is coupled with the distal inner body 26. The stabilizing wire 34 may of course be made of various materials, including stainless steel, nitinol, or any other biocompatible material with a relatively high column strength. Likewise, the stabilizing wire 34 need not even be a wire, but is preferably a stainless steel tubular hypotube. At its proximal end, the stabilizing wire 34 is connected to the second hub 22, which provides a maneuvering handle for a physician to operate the device.

The distal shaft section 16 may include a distal inner body 26, extending from a proximal end where it is coupled with the stabilizing wire 34, to a distal end where the stent 24 is mounted and the flexible tapering tip 18 is attached. The distal inner body 26 is preferably tubular and defines guidewire lumen 36 for receiving an elongated flexible guidewire 38 in a sliding fashion, which extends the full length of the inner body 26.

The stent 24 is preferably of the self-expanding type, usually a tubular structure resiliently tending to expand from a first delivery diameter to a second deployed diameter. There are of course a wide variety of stent designs which are acceptable for the stent delivery system of the present invention. One possible design is a stent made of nitinol metal wire that is bent and wound into the desired shape. A second possible design is a stent made of a cylindrical tube that is selectively cut to form a flexible tubular lattice.

Accordingly, a self-expanding stent 24 of suitable type or configuration is preferably provided with the rapid exchange stent delivery system of the present invention, such as the SMART Stent, available from Cordis Corporation, Miami, Fla. Various kinds and types of self-expanding stents are acceptable for use in the present invention, as well as new stents which may be developed in the future that are compatible with the present stent delivery system. When deployed in a body passageway of a patient, the stent is preferably designed to press radially outward to hold the passageway open.

The stent cartridge 28 is affixed to the distal end of the distal outer body 30, and surrounds the compressed stent 24 during delivery to the desired site. When the stent 24 is in position, the cartridge 28 is withdrawn to expose and deploy the stent 24. The outer body 30 extends from and is connected to the transition tube 46 and the cartridge 28. It is permanently mounted about the inner body 26, yet is able to slide a short distance longitudinally back and forth relative to the inner body 26. The guidewire 38 and stent delivery system 10 may thus be advanced or withdrawn independently, or the catheter 12 may be guided along a path selected with the guidewire 38.

The stent delivery system 10 of the present invention further has a flexible tapering introducer tip 18, adapted to help cross and traverse lesions or stenoses. Prior catheter designs tend toward very small profiles at their distal tips, with the understanding that a small profile might assist in crossing a narrow lesion. This profile is simply defined by the outer diameter of the inner tube at its distal end, which may even be drawn down to an even smaller diameter. All dimensions in this application are expressed in inches, except where indicated otherwise.

The introducer tip 18 may be affixed to the distal end of the guidewire tube 12 by any appropriate method that provides secure attachment, including an adhesive or by heat welding. The material selection of the introducer tip 18 should be selected such that it is more flexible than the distal end of the inner body 26, even though the inner body 26 is smaller in diameter. This enhanced flexibility of the introducer tip 18 should preferably cooperate with its gently tapering slope to accurately follow the desired vascular path while minimizing the occurrence of any possible vascular trauma or complication, and may tend to gently widen a stenosis or push aside thrombus.

Structurally, the introducer tip 18 as shown in the drawings preferably has a tapering conical main surface 54 at its distal end, and a short cylindrical transition surface 56. The introducer tip 18 also has a short collar 76 with a slightly smaller outer diameter, and a novel reverse tapering surface 74 which may tend to reduce or minimize any possible affect on the anatomy when withdrawing the catheter system from the patient. The introducer tip 18 receives and is affixed to the distal end of the inner body tube 12. The flexibility of the introducer tip 18 should be optimized to enable the stent delivery system 10 to accurately follow the guidewire 38 without causing prolapse.

Various different materials may be used for the various components of a stent delivery system according to the present invention. Most of the catheter components should preferably be made of materials having acceptable properties including biocompatibility, pull strength, longitudinal or column strength, and bending flexibility. Some of the preferred materials may include various plastics, referred to as polymers, including nylon, polyethylenes, polyurethanes, or PET.

For example, the guidewire is preferably made of metal such as stainless steel, while the proximal shaft, inner body, outer body, cartridge, tapered tip, transition tube, and joinder sleeve may be of polymers. The stabilizing wire should be of course have enhanced column strength, and may be made of metal.

In the particular preferred embodiment shown in the drawings, a specific set of materials has been selected. The tapered tip 18 may be of nylon or similar material. The inner body 26 and the cartridge 28 are preferably a sandwich of multiple polymer layers with a reinforcing metal coil or braid 58, for example outer and inner layers of polyimide with stainless steel coil or braid in between. A lubricious coating, for example PTFE, may be added.to the inner guidewire lumen 36 of the inner body 26.

Likewise, outer body 30 is preferably also a co-extrusion or layered construction, with outer and inner polymer layers 78 and 80. Polymer layer 78 may for example be nylon, and inner layer 80 may be polyethylene.

The inner body 26 preferably has a radiopaque marker 68 adjacent to the proximal end of the stent 24, which preferably defines an outwardly extending surface for resisting motion of the stent 24 as the stent cartridge 28 is retracted.

Inner body 26 may also have a second radiopaque marker 70 adjacent to the distal end of the stent 24. Radiopaque markers 68 and 70 are visible with fluoroscopy during medical catheter procedures, enabling a physician to see the stent ends with x-rays.

In addition, a radiopaque tip marker 72 may preferably be attached to the flexible tapered tip 18, for illustrating more accurately where the distal tip of the catheter system 12 is in the patient's body.

The stent cartridge 28 may include several novel features, such as a distal cartridge marker 60 of radiopaque material sandwiched between polymer layers 62 and 64. Also, a portion of the cartridge inner layer 64 may be removed near its proximal end, for any of several reasons: to prevent overlap, to aid in bonding cartridge 28 to outer body 30, and to minimize the outer profile of the stent delivery system.

Various radiopaque materials are available for the markers 60, 68, 70 and 72 including gold, iridium, and platinum.

The outer body 30 is preferably a polymer construction, for example nylon or polyethylene, or a co-extrusion of nylon surrounding polyethylene. Some examples include Nylon, PEEK, the polymer sold under the trade name PEBAX material, or a block copolymer thereof.

The distal end of the stabilizing wire 34 is affixed to the proximal end of the inner body 26, which may be accomplished with a joinder sleeve 66 surrounding them. This joinder sleeve seal may of course be accomplished by a variety of sealing techniques, including heat-sealing or an adhesive. The stabilizing wire 34 is preferably "coined" as shown in FIG. 4, in which the cross-section of the stabilizing wire 34 distal end is deformed to become a crescent shape, thus meshing with the cylindrical wall of the inner body 26. This coining feature further provides for strength and low profile at the transition.

The cartridge 16 is permanently mounted about the catheter shaft inner body 12, but is generally free to slide longitudinally a short distance with outer body 30. To accomplish this feature, the first hub 22 allows the catheter shaft 24 to slidably.withdraw along the stabilizing wire, and also preferably has the threaded screw-down locking device 52 for resisting relative motion. As an alternative embodiment, a proximal portion of the stabilizing wire may be formed or jacketed by a metal hypotube.

Figure 6:
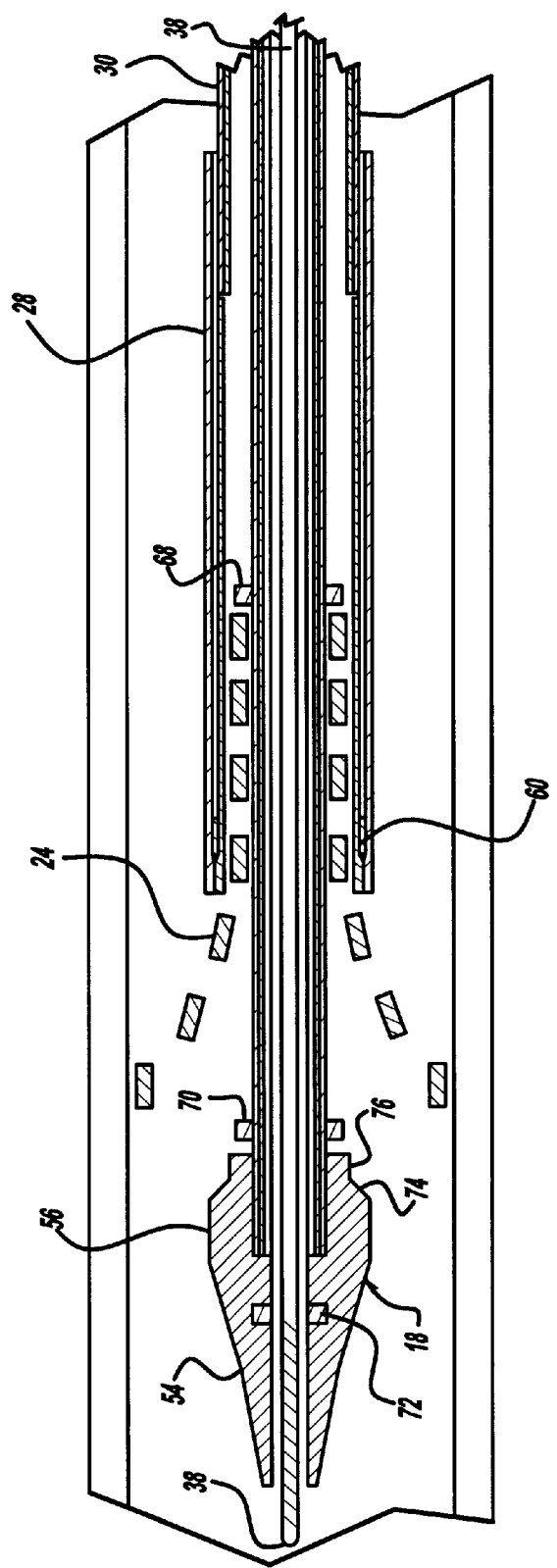
FIG. 6 is a partial longitudinal cross-section view of the stent delivery system of FIG. 5, in which the sheath is partially retracted to uncover the stent.
Figure 7:
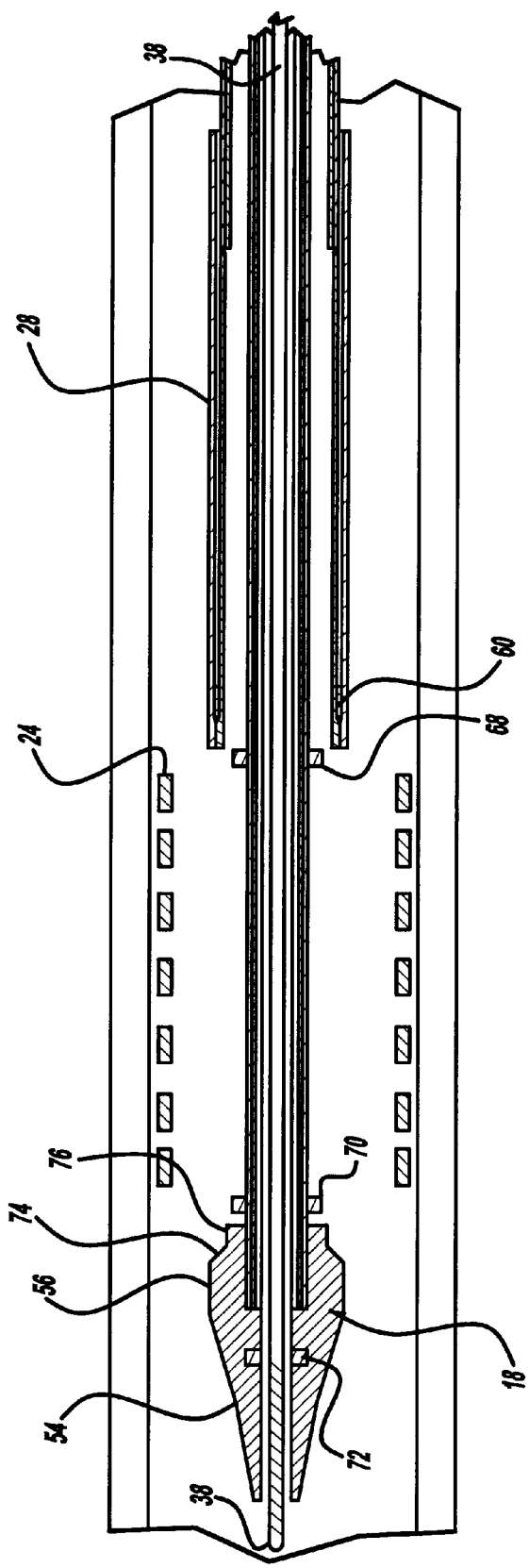
FIG. 7 is a partial longitudinal cross-section view of the stent delivery system of FIG. 6, in which the sheath is retracted to expose and deploy the stent.
Figure 8:
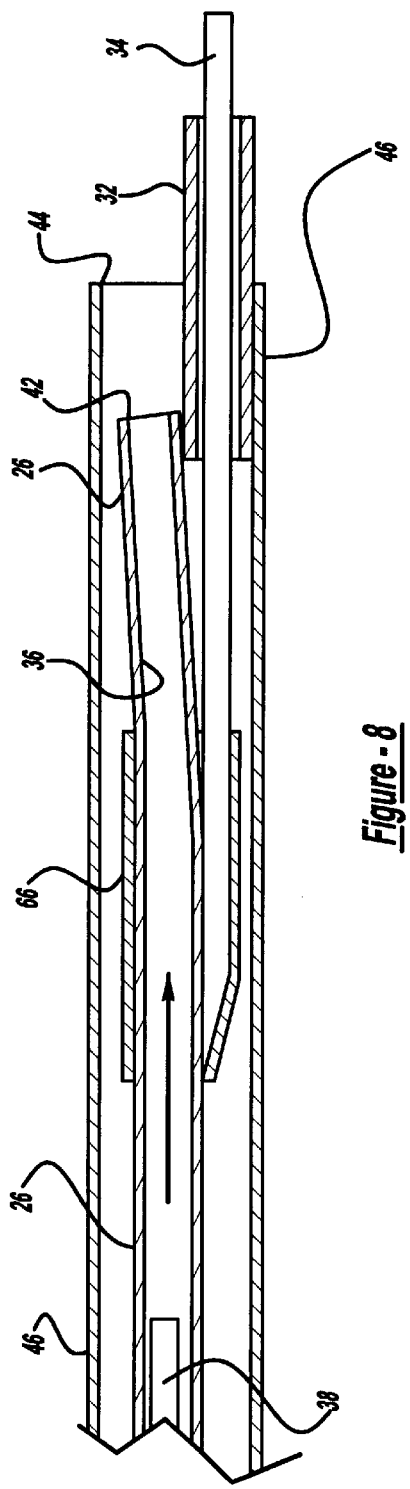
FIG. 8 is a longitudinal cross-section view of the stent delivery system of FIG. 5, illustrating back-loading of the guidewire.
Figure 9:
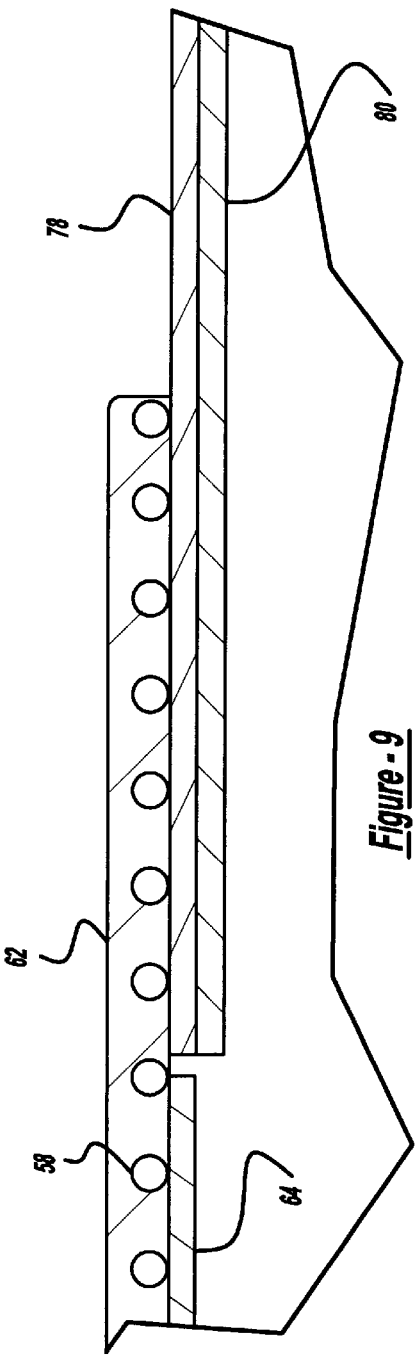
FIG. 9 is a partial detail cross-section view of a portion of a stent delivery system.

The operation of the stent delivery system 10 is depicted in diagram form in FIGS. 5–8. The stent delivery system 10 may be first back-loaded onto a guidewire 38 already positioned along the body passage to the desired site, by inserting a proximal end of the guidewire 38 into distal guidewire port 40. The guidewire 38 proceeds in the proximal direction of the arrow in FIG. 8, and is smoothly and easily guided through the inner and outer proximal guidewire ports 42 and 44. The stent delivery system 10 may be inserted percutaneously through an outer guiding catheter (not shown) and along a guidewire already positioned along the body passage to the desired site. The stent delivery system 10 is then advanced along the guidewire 38, until the stent 24 covered by the cartridge 28 is positioned within the lesion (not shown).

The sheath 30 is then partially retracted by unlocking screwlock 52, holding second hub 22 in place, and withdrawing first hub 20 in a proximal direction toward the second hub 22. This action causes the proximal shaft tube, transition tube, outer body and stent cartridge to be pulled back a short distance proximally, to uncover the stent as in FIG. 6. The stent delivery system 12 is removed from the patient's body after full deployment as in FIG. 7, leaving the stent 24 implanted at the desired site.

Catheter manufacturing techniques are generally known in the art, including extrusion and co-extrusion, coating, adhesives, and molding. The scope of the present invention encompasses the full extent of the claims, regardless of specific numbers, materials, or other details present in this description of the preferred embodiment.

Preferably, the catheter hub 20 and 22 are injection molded of any suitable material. The inner and outer shaft tubes 26 and 30 are preferably made of a polymer such as Nylon, the material stiffness of which may be selected as appropriate.

It should be understood that an unlimited number of configurations for the present invention could be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A self expanding stent deployment system having a rapid exchange configuration, comprising:

a catheter system having proximal and distal ends, with an elongated flexible shaft having proximal and distal shaft sections, and a self-expanding tubular stent mounted about the shaft near the shaft distal end;

a tubular inner and outer body forming at least a portion of the distal shaft section, the tubular inner body defining a guidewire lumen, the tubular outer body surrounding a portion of the inner body, a tubular stent cartridge affixed to a distal end of the outer body, and a flexible tapered tip affixed to a distal end of the inner body; wherein the stent cartridge surrounds and compresses the self-expanding stent during a first initial configuration, in which a distal end of the stent cartridge is disposed near the tapered tip; wherein the guidewire lumen extends from a distal guidewire port defined by the tapered tip to an inner proximal guidewire port defined at the proximal end of the inner body, and then to an outer proximal guidewire port;

the proximal shaft section having a proximal shaft tube with a proximal end affixed to a first proximal hub, and a stabilizing wire extending through the proximal shaft tube and having a proximal end affixed to a second proximal hub; wherein the first and second hubs are separated by a predetermined distance during the initial configuration;

a transition tube joining the proximal and distal shaft sections, having a proximal end affixed to the proximal shaft tube near its distal end, and having a distal end affixed to the outer body near its proximal end; the outer proximal guidewire port being defined by an interface between the proximal end of the transition tube and a distal end portion of the proximal shaft tube;

wherein a distal end of the stabilizing wire is affixed to the inner body near its proximal end;

the catheter system having a second deployed configuration, in which the first hub is selectively pulled back in the proximal direction toward the second hub; such that the proximal shaft tube, the transition tube, the outer body, and the stent cartridge are all successively pulled back in the proximal direction, to fully uncover and release the self-expanding stent;

wherein during the initial configuration, some portion of the lengths of the proximal shaft tube and the inner body overlap;

wherein during both the initial and deployed configurations, the outer proximal guidewire port is proximal from the proximal end of the inner body, such that guidewire lumen defines a cross-sectional area, and the guidewire lumen cross-sectional area is constant or expanding when measured in the proximal direction throughout its length to the outer proximal guidewire port; thereby facilitating back-loading of the guidewire into the distal guidewire port and out through the inner and outer guidewire ports.

2. The stent delivery system of claim 1, wherein the inner and outer proximal guidewire ports each have a minimal length along a longitudinal axis of the catheter system, to maximize the pull strength and column strength of the catheter system, and to smooth transitions in bending flexibility in the region of the catheter system near the transition.

3. The stent delivery system of claim 1, further comprising a flush port defined by the first proximal hub, communicating with a flush lumen defined by the proximal shaft tube, the transition tube, the outer body and the stent cartridge, so that a liquid can be injected into the flush port and through the flush lumen.

4. The stent delivery system of claim 1, further comprising a locking device coupled with the first hub and having a locked configuration and a released configuration, selectively resisting motion of the first hub with respect to the second hub during the locked configuration.

5. The stent delivery system of claim 1, wherein the stent is formed of an integral unitary metal cylinder having a multitude of portions removed, to form a lattice.

6. The stent delivery system of claim 1, wherein the stabilizing wire is formed of solid metal wire, a distal portion of the stabilizing wire having a crescent shape; a concave portion of the crescent shape matching and cooperating with a cylindrical outer wall of the distal inner body at a joint location where the stabilizing wire is connected to the inner body; such that a maximum lateral dimension of the stabilizing wire and distal inner body is reduced at the joint location.

7. The stent delivery system of claim 6, wherein the distal end of the stabilizing wire and a portion of the inner body near its proximal end are held together at the joint location by a joinder sleeve surrounding a portion of both the stabilizing wire and inner body.

8. The stent delivery system of claim 1, further comprising a radiopaque proximal marker affixed to the inner body at a position proximal from and adjacent to a proximal end of the stent, the marker defining a shoulder for contacting the proximal end of the stent, thereby resisting proximal motion of the stent during withdrawal and retraction of the stent cartridge for deployment of the stent.

9. The stent delivery system of claim 8, further comprising a radiopaque distal marker affixed to the inner body at a position distal from and adjacent to a distal end of the stent.

10. The stent delivery system of claim 1, further comprising a radiopaque tip marker affixed to the tapered tip.

11. The stent delivery system of claim 10, wherein the entire radiopaque tip marker is surrounded by some portion of the tapered tip.

12. The stent delivery system of claim 1, further comprising a radiopaque cartridge marker affixed to a distal end of the stent cartridge.

13. The stent delivery system of claim 1, wherein the tip has a leading surface that is tapered from a relatively narrow distal end to a broader tip body portion having outer dimensions similar to the outer dimensions of the stent cartridge; wherein the tip further comprises a cylindrical surface sized to match an inner dimension of the distal end of the stent cartridge, wherein the tip further has an auxiliary tapering surface facing proximally and tapering from the tip body portion to the smaller cylindrical surface; such that the tip provides a gentle tapering surface that tends to minimize any possible trauma to the anatomy during withdrawal of the catheter system.

14. The stent deployment system of claim 1, wherein the stent is formed of one or more wires arranged into an integral non-unitary metal cylinder having one or more attachments between selected portions of the wires.

15. The stent deployment system of claim 1, wherein said inner body, outer body, and proximal shaft tube are formed of a material selected from the group consisting of nylon, polyethylene, polyimide, polyamide, or a block copolymer thereof.

16. The stent deployment system of claim 1, wherein the stabilizing wire comprises a length of metal hypotube.

17. A catheter system having a rapid-exchange configuration, comprising:

an elongated flexible shaft having proximal and distal shaft sections, the distal shaft section having a tubular inner body defining a guidewire lumen, a tubular outer body surrounding a portion of the inner body;

wherein the guidewire lumen extends from a distal guidewire port near a distal end of the catheter to an inner proximal guidewire port defined at the proximal end of the inner body, and then to an outer proximal guidewire port;

the proximal shaft section having a proximal shaft tube;

a transition joining the proximal and distal shaft sections, having a proximal end affixed to the proximal shaft tube near its distal end, and having a distal end affixed to the outer body near its proximal end; the outer proximal guidewire port being defined by an interface between the proximal end of the transition tube and a distal end portion of the proximal shaft tube;

wherein the inner and outer proximal guidewire ports are near each other at a predetermined distance during an initial configuration;

wherein during the initial configuration, some portion of the lengths of the proximal shaft tube and the inner body overlap;

the catheter system having a second deployed configuration, in which the proximal shaft tube is selectively pulled back in the proximal direction; such that the proximal shaft tube, the transition tube, and the outer body are all successively pulled back in the proximal direction;

wherein during both the initial and deployed configurations, the outer proximal guidewire port is proximal from the proximal end of the inner body; such that guidewire lumen defines a cross-sectional area, and the guidewire lumen cross-sectional area is constant or expanding when measured in the proximal direction throughout its length to the outer proximal guidewire port; thereby facilitating back-loading of the guidewire into the distal guidewire port and out through the inner and outer guidewire ports.

* * * * *